(12) United States Patent
Auberson et al.

(10) Patent No.: US 7,632,851 B2
(45) Date of Patent: Dec. 15, 2009

(54) BENZO[1,2,5]OXADIAZOLES AND BENZOL[1,2,5]THIADIAZOLES USEFUL AS HISTOPATHOLOGICAL STAINING AGENTS, IMAGING AGENTS AND BIOMARKERS

(75) Inventors: Yves Auberson, Allschwil (CH); Samuel Hintermann, Basel (CH); Kaspar Zimmermann, Oberwil BL (CH)

(73) Assignee: Novartis AG, Basel (CH)

( * ) Notice: Subject to any disclaimer, the term of this patent is extended or adjusted under 35 U.S.C. 154(b) by 273 days.

(21) Appl. No.: 10/549,248

(22) PCT Filed: Apr. 2, 2004

(86) PCT No.: PCT/EP2004/003517

§ 371 (c)(1), (2), (4) Date: Nov. 16, 2005

(87) PCT Pub. No.: WO2004/087684

PCT Pub. Date: Oct. 14, 2004

(65) Prior Publication Data

US 2006/0093551 A1    May 4, 2006

(30) Foreign Application Priority Data

Apr. 4, 2003 (GB) .................................. 0307855.7

(51) Int. Cl.
*A61K 31/4245* (2006.01)
*A61K 31/41* (2006.01)
*A61K 31/433* (2006.01)
*C07D 285/02* (2006.01)
*C07D 271/12* (2006.01)

(52) U.S. Cl. .................. 514/362; 514/361; 514/364; 548/125; 548/134

(58) Field of Classification Search ................. 514/361, 514/362, 364; 548/125, 134
See application file for complete search history.

(56) References Cited

FOREIGN PATENT DOCUMENTS

EP        1 110 945        6/2001
WO       WO 00/10614      3/2000

OTHER PUBLICATIONS

Domschke, G. "ESR Study of the Reaction of Trithiazyl Trichloride with Primary Aromatic Amines." Magnetic Resonance in Chemistry 28(1990): 797-806.*
Patent Abstracts of Japan, vol. 1999, No. 13, (1999) & JP 11 228550 (1999).

* cited by examiner

*Primary Examiner*—Kamal A Saeed
*Assistant Examiner*—Samantha L Shterengarts
(74) *Attorney, Agent, or Firm*—Paul D. Strain; Fanelli, Strain & Haag, PLLC

(57) ABSTRACT

The present invention relates to novel benzo[1,2,5]oxadiazoles and benzo[1,2,5]thiadiazoles of formula (I) wherein X is O or S, $R_1$ is 5-(2-fluoro-ethylamino)-thiazol-2-yl, 5-(2-$^{18}$F-ethylamino)-thiazol-2-yl or a group of formula (a) wherein Y is CH or N, $R_2$ is $NHCH_3$, $NH^{11}CH_3$, $N(CH_3)^{11}CH_3$, $N(CH_3)_2$, $N(^{11}CH_3)_2$, $NH(CH_2)_nF$, $NH(CH_2)_n^{18}F$, $N(CH_3)(CH_2)_nF$, $N(CH_3)$—$(CH_2)_n^{18}F$, O—$(CH_2)_nF$, O—$(CH_2)_n^{18}F$, $CONH(CH_2)nF$ or $CONH(CH_2)_n^{18}F$ (n being in each case 2 to 4) and $R_3$ is hydroxy, (C1-4)alkoxy, hydrogen or nitro, in free base or acid addition salt form; their preparation, their use as markers in diagnosis and compositions containing them.

14 Claims, No Drawings

BENZO[1,2,5]OXADIAZOLES AND BENZOL[1,2,5]THIADIAZOLES USEFUL AS HISTOPATHOLOGICAL STAINING AGENTS, IMAGING AGENTS AND BIOMARKERS

The present invention relates to novel benzo[1,2,5]oxadiazoles and benzo[1,2,5]thiadiazoles, their preparation, their use as markers and compositions containing them.

More particularly the invention provides a compound of formula I

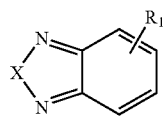

I wherein X is O or S, $R_1$ is 5-(2-fluoro-ethylamino)-thiazol-2-yl, 5-(2-$^{18}$F-ethylamino)-thiazol-2-yl or a group of formula (a)

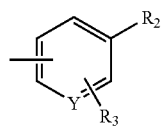

(a)

wherein Y is CH or N, $R_2$ is $NHCH_3$, $NH^{11}CH_3$, $N(CH_3)$ $^{11}CH_3$, $N(CH_3)_2$, $N(^{11}CH_3)_2$, $NH(CH_2)_nF$, $NH(CH_2)_n$$^{18}F$, $N(CH_3)$—$(CH_2)_nF$, $N(CH_3)$—$(CH_2)_n$$^{18}F$, $O$—$(CH_2)_nF$, $O$—$(CH_2)_n$$^{18}F$, $CONH(CH_2)_nF$ or $CONH(CH_2)_n$$^{18}F$ (n being in each case 2 to 4) and $R_3$ is hydroxy, $(C_{1-4})$alkoxy, hydrogen or nitro, in free base or acid addition salt form.

The term (C1-4)alkoxy as used herein relates to a radical comprising an alkyl moiety with from and including 1 up to and including 4 C atoms and is linear or branched; preferably (C1-4)alkoxy is methoxy, ethoxy or n-propoxy.

Natural occurring carbon consists of the isotopes $^{12}$C (98.90%), $^{13}$C (1.10%) and traces of $^{14}$C. The term "$^{11}$C" denotes that a higher ratio of the respective carbon atoms in a radical or moiety correspond to $^{11}$C isotopes as compared to natural occurring carbon, especially a radical or moiety wherein at least 25%, preferably at least 90%, more preferably at least 95%, of the carbon atoms are $^{11}$C isotopes.

The $^{11}$C isotope can be prepared by methods known as such. Since the half-life period is short (about 20 min), the isotope needs to be freshly prepared shortly before usage in reagents by employment of a cyclotron. The methylation reaction using $^{11}$C-methyl iodide is the most used reaction in $^{11}$C labelling synthesis. A suitable method is based on the reduction of trapped $^{11}$C-carbon dioxide with lithium aluminumhydride in tetrahydrofuran, followed by removal of solvent. Hydroiodic acid is added and the formed $^{11}$C-methyl iodide distilled in a stream of nitrogen gas to the reaction flask.

Natural occurring fluorine consists of the isotope $^{19}$F (100%). The term "$^{18}$F" denotes that a higher ratio of the respective fluorine atoms in a radical or moiety correspond to $^{18}$F isotope as compared to natural occurring fluorine, especially a radical or moiety wherein at least 25%, preferably at least 90%, more preferably at least 95%, of the fluorine atoms are $^{18}$F isotopes.

The $^{18}$F isotope can be prepared by methods known as such. Since the half-life period is short (about 110 min), the isotope needs to be freshly prepared shortly before usage in reagents by employment of a cyclotron. $^{18}$F can be obtained, e.g., by irradiating a target containing $^{18}$O—$H_2O$ with a proton beam, in a cyclotron. In this process, $^{18}$F is obtained from the $^{18}$O(p,n) $^{18}$F nuclear reaction and used immediately to generate final radiomarkers as described, e.g. in "Fundamentals of Positron Emission tomography and Applications in Preclinical Drug Development", Simon R Cherry, J Clin Pharmacol 2001; 41:482-491, and the references cited therein, which publication is included in the present patent filing by reference.

For diagnostic purposes, those compounds of formula I are preferred comprising $^{11}$C or $^{18}$F.

In a further aspect, the invention provides a process for the production of the compounds of formula I and their salts, comprising the steps of a) for the production of a compound of formula I which contains no $^{11}$C or $^{18}$F atom, reacting a compound of formula II

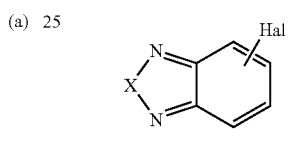

II wherein X is as defined above and Hal is Cl, Br or I, with 5-(2-fluoro-ethylamino)thiazolyl-2-boronic acid or a compound of formula III

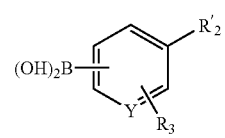

III wherein Y and $R_3$ are as defined above and $R'_2$ is a group $R_2$ as defined above which contains no $^{11}$C or $^{18}$F atom, or b) for the production of a compound of formula I wherein $R_1$ is 5-(2$^{18}$F-ethylamino)-thiazol-2-yl, reacting a compound of formula I wherein $R_1$ is 5-(2-mesyloxy-ethylamino)-thiazol-2-yl or 5-(2-tosyloxy-ethylamino)-thiazol-2-yl with $^{18}$F⊖, or c) for the production of a compound of formula I wherein $R_2$ is $NH^{11}CH_3$, $N(CH_3)^{11}CH_3$ or $N(^{11}CH_3)_2$, reacting a compound of formula I wherein $R_2$ is $NH_2$ or $NHCH_3$ with $^{11}CH_3I$, or d) for the production of a compound of formula I wherein $R_2$ is $NH(CH_2)_n$$^{18}F$, $N(CH_3)$—$(CH_2)_n$$^{18}F$, $O$—$(CH_2)_n$$^{18}F$ or $CONH(CH_2)_n$$^{18}F$, reacting a compound of formula I wherein $R_2$ is, respectively, $NH(CH_2)_n$OTs or $NH(CH_2)_n$OMs, $N(CH_3)$—$(CH_2)_n$OTs or $N(CH_3)$—$(CH_2)_n$—OMs, $O$—$(CH_2)_n$OTs or $O$—$(CH_2)_n$—OMs, or $CONH(CH_2)_n$OTs or $CONH(CH_2)_n$OMS, with $^{18}$F⊖, and recovering the resulting compound of formula I in free base form or in form of an acid addition salt.

The reaction described under a) can be effected according to known methods, for example as described in Example 1.

Alternatively to process a), conventional methods can be used for the production of compounds of formula I which contain no $^{11}$C or $^{18}$F atom, for example as described in Examples 4, 7 and 13 to 25.

The reactions described under b), c) and d) can be effected according to conventional methods.

Working up the reaction mixtures and purification of the compounds thus obtained may be carried out in accordance to known procedures.

Acid addition salts may be produced from the free bases in known manner, and vice-versa.

The agents of the invention have a high affinity to β-amyloid deposits, especially extracellular β-amyloid deposits, and bind to these deposits by means of physical or chemical interaction.

Hence, the agents of the invention can be used in the therapy or diagnosis of diseases wherein such β-amyloid deposits are observed, such as Alzheimer's Disease. Preferably, the agents of the invention are used in diagnosis.

In particular, compounds of formula I in free base or acid addition salt form, hereinafter referred to as agents of the invention, exhibit valuable properties as histopathological staining agents, imaging agents and/or biomarkers, hereinafter "markers".

More particularly, the agents of the invention are useful as markers for labeling pathological structures such as extracellular β-amyloid deposits, e.g. in the brain of patients with Alzheimer's disease (see Example 26).

The agents of the invention are therefore useful for the early diagnosis and prevention of Alzheimer's disease and for monitoring the effectiveness of therapeutic treatments of Alzheimer's disease.

The advantages of assessing amyloid deposits in vivo and non-invasively using markers capable of labeling these structures have been reported e.g. in WO 00/10614, which is incorporated herein by reference.

In accordance with the above, the present invention provides a composition for labeling histopathological structures in vivo or in vitro, comprising an agent of the invention.

In a further aspect, the present invention provides a method for labeling histopathological structures in vitro or in vivo, which comprises contacting brain tissue with an agent of the invention.

Said brain tissue comprises for example β-amyloid deposits.

Contacting the brain tissue with the agent of the invention is for example effected by administering the agent of the invention to a patient, e.g. a patient with Alzheimer's disease.

The method of the invention may comprise a further step aimed at determining whether the agent of the invention labeled the target structure.

If the agent of the invention is a non-radioactive compound of formula I, said further step may be effected by observing the target structure using fluorescence microscopy.

If the agent of the invention is a radioactive compound of formula I, said further step may be effected by observing the target structure using positron emission tomography (PET).

Labeling histopathological structures in vitro is effected, for example, for detecting histopathological hallmarks of Alzheimer's disease.

Labeling histopathological structures in vivo is effected, for example, for diagnosing Alzheimer's disease in a patient or for monitoring the effectiveness of a therapeutic treatment of Alzheimer's disease.

In further aspects, the present invention relates to the use of a compound of formula I for the manufacture of a preparation for the treatment or diagnosis of Alzheimer's disease;

a package comprising a compound of formula I wherein $R_2$ is $NH_2$ or $NHCH_3$ together with instructions for the production of a compound of formula I wherein $R_2$ is $NH^{11}CH_3$, $N(CH_3)^{11}CH_3$ or $N(^{11}CH_3)_2$ by reaction of the starting material with freshly prepared $^{11}CH_3I$; and to a package comprising as starting material a compound of formula I wherein $R_2$ is $NH(CH_2)_n OTs$, $NH(CH_2)_n OMs$, $N(CH_3)$—$(CH_2)_n OTs$, $N(CH_3)$—$(CH_2)_n OMs$, $O$—$(CH_2)_n OTs$, $O$—$(CH_2)_n$—$OMs$, $CONH(CH_2)_n OTs$ or $ONH(CH_2)_n OMs$, wherein OMs corresponds to mesylate and OTs to tosylate, together with instructions for the production of a compound of formula I wherein $R_2$ is $NH(CH_2)_n{}^8F$, $N(CH_3)$—$(CH_2)_n{}^{18}F$, $O$—$(CH_2)_n{}^{18}F$ or $CONH(CH_2)_n{}^{18}F$ by a suitable reaction cascade of the starting material with $^{18}F\ominus$.

The following Examples illustrate the invention.

Abbreviations

Boc t-butoxycarbonyl

DMAP dimethylamino pyridine

DMF dimethyl formamide

DMSO dimethyl sulfoxide

Dppf 1,1'-bis(diphenylphosphino)ferrocene

EDC N-(3-dimethylaminopropyl)-N'-ethylcarbodiimide

Eq. equivalents

HOBt 1-hydroxybenzotriazole

HPLC high pressure liquid chromatography

NaHMDS sodium hexamethyldisilazane

NMR nuclear magnetic resonance

OMs mesylate

OTs tosylate

THF tetrahydrofurane

EXAMPLE 1

(4-Benzo[1,2,5]oxadiazol-5-yl-phenyl)-dimethylamine 500 mg (2.5 mmol) 5-bromo-benzo[1,2,5]oxadiazole and 313 mg (0.1 eq.) tetrakis-(triphenylphosphine)palladium are stirred for 30 minutes at room temperature in 10 mL 1,2-dimethoxyethane. 533 mg (2 eq.) sodium carbonate are dissolved in 1.8 mL water and added to the reaction mixture, followed by 663 mg (1.6 eq.) 4-(dimethylamino)phenylboronic acid. After stirring at reflux for 18 h, the reaction mixture is cooled to room temperature and extracted with ethyl acetate and water. The organic phases are combined, dried with magnesium sulfate, filtered and evaporated. The residue is column chromatographed (hexane, then hexane/ethyl acetate 8:1 then 5:1) to yield the desired product as a yellow solid. MS(ES+): 240 (M+1).

$^1$H-NMR (CDCl$_3$, 400 MHz): delta (ppm)=7.83 (d, H$_{arom}$); 7.82 (s, H$_{arom}$); 7.73 (d, H$_{arom}$); 7.58, 6.81 (2d, 2×2H$_{arom}$); 3.05 (s, 2Me).

The following compounds of examples 2 to 6 can be prepared according to the same procedure:

EXAMPLE 2

(4-Benzo[1,2,5]thiadiazol-4-yl-phenyl)-dimethyl-amine

Starting from 4-iodo-benzo[1,2,5]thiadiazole and 4-(dimethylamino)phenylboronic acid. Orange powder. MS(ES+): 256 (M+1).

EXAMPLE 3

(4-Benzo[1,2,5]oxadiazol-4-yl-phenyl)-dimethyl-amine

Starting from 4-chloro-benzo[1,2,5]oxadiazole and 4-(dimethylamino)phenylboronic acid. Orange powder. MS(ES+): 240 (M+1).

EXAMPLE 4

(3Benzo[1,2,5]oxadiazol-5-yl-phenyl)-methyl-amine

Starting from 5-benzo[1,2,5]oxadiazoleboronic acid and (3-bromo-phenyl)-methyl-amine. Yellow powder. MS(ES+): 226 (M+1).

EXAMPLE 5

5-[4-(2-Fluoro-ethoxy)-phenyl]-benzo[1,2,5]oxadiazole

Starting from 5-benzo[1,2,5]oxadiazoleboronic acid and 1-bromo-4-(2-fluoro-ethoxy)-benzene. Yellow-beige powder. MS(ES+): 259 (M+1).

EXAMPLE 6

(3-Benzo[1,2,5]oxadiazol-5-yl-phenyl)-dimethyl-amine

Starting from 5-benzo[1,2,5]oxadiazoleboronic acid and (3-bromo-phenyl)-dimethyl-amine. Orange-yellow powder. MS(ES+): 240 (M+1).

EXAMPLE 7

(2Benzo[1,2,5]oxadiazol-5-yl-phenyl)-dimethyl-amine 523 mg (1.65 eq.) bis(pinacolato)diboran, 552 mg (4.5 eq.) potassium acetate and 51 mg (0.01 eq.) PdCl(dppf)-$CH_2Cl_2$ are added to a solution of 373 mg 5-bromo-benzo[1,2,5]oxadiazole in 8 mL DMF and heated to 80° C. under continuous stirring for 6 hours. 662 mg (5 eq.) sodium carbonate in 3.3 mL water are added together with 500 mg (1 eq.) 2-bromo-N,N-dimethylaniline and 51 mg (0.01 eq.) PdCl(dppf)-$CH_2Cl_2$ to the reaction mixture, which is stirred for another 18 hours at 80° C., cooled to room temperature and extracted with ethyl acetate and water. The combined organic phases are washed with brine, dried over magnesium sulfate and evaporated. The residue is column chromatographed (hexane, then hexane/ethyl acetate 8:1) to yield the desired product as an orange resin. MS(ES+): 240 (M+1).

$^1$H-NMR ($CDCl_3$, 400 MHz): delta (ppm)=7.77 (s, $H_{arom}$); 7.71, 7.69 (2d, $2H_{arom}$); 7.25, 7.03 (2m, $2 \times 2H_{arom}$); 2.53 (s, 2Me).

The following compounds of Examples 8 to 12 are synthesized according to the same procedure:

EXAMPLE 8

(2Benzo[1,2,5]thiadiazol-5-yl-phenyl)-dimethyl-amine

Starting from 5-bromo-benzo[1,2,5]thiadiazole and 2-bromo-N,N-dimethylaniline. Orange resin. MS(ES+): 256 (M+1).

EXAMPLE 9

(3Benzo[1,2,5]oxadiazol-4-yl-phenyl)-methyl-amine

Starting from 5-chloro-benzo[1,2,5]oxadiazole and (3-bromo-phenyl)-methyl-amine. Yellow powder. MS(ES+): 226 (M+1).

The starting material is obtained as follows:

(3-Bromo-phenyl)-methyl-amine 2 g (11.6 mmol) 3-Bromoaniline is dissolved in 15 mL DMF and treated with 716 mg (1.1 eq.) KOH and 0.722 mL (1 eq.) iodomethane under continuous stirring at room temperature for 20 hours. The reaction mixture is extracted with ethyl acetate and water, the combined organic phases are washed with brine and dried with sodium sulfate and evaporated to dryness. The residue is column chromatographed (ethyl acetate/petroleum ether 2:5) to yield after evaporation the desired product as a yellow oil.

EXAMPLE 10

4-[4-(2-Fluoro-ethoxy)-phenyl]-Benzo[1,2,5]oxadiazole

Starting from 4-chloro-benzo[1,2,5]oxadiazole and 1-bromo-4-(2-fluoro-ethoxy)-benzene. Yellow crystals. MS(ES+): 259 (M+1).

EXAMPLE 11

5Benzo[1,2,5]oxadiazol-5-yl-N-(2-fluoro-ethyl)-nicotinamide

Starting from 5-bromo-benzo[1,2,5]oxadiazole and 5-bromo-N-(2-fluoro-ethyl)-nicotinamide. Beige powder. MS(ES−): 285 (M−1).

The starting material is obtained as follows:

5-Bromo-N-(2-fluoro-ethyl)-nicotinamide 2.03 g (10 mmol) 5-bromonicotinic acid, 1 g (1 eq.) 2-fluoroethylamine, 2.31 g (1.2 eq.) EDC.HCl, 123 mg (0.1 eq.) DMAP and 5.6 mL (4 eq.) triethylamine are stirred in 60 mL dichloromethane for 20 hours at room temperature. The reaction mixture is extracted with dichloromethane and water, the combined organic phases are washed with brine, dried with sodium sulfate and evaporated. The residue is triturated in diethylether and hexane to yield after filtration the desired product as a white powder. MS(ES+): 347 and 349 (M+1).

EXAMPLE 12

4Benzo[1,2,5]oxadiazol-5-yl-N-(2-fluoro-ethyl)-nicotinamide

Starting from 4-chloro-benzo[1,2,5]oxadiazole and 5-bromo-N-(2-fluoro-ethyl)-nicotinamide. Beige powder. MS(ES−): 285 (M−1).

EXAMPLE 13

(4Benzo[1,2,5]oxadiazol-5-yl-phenyl)-methyl-amine 510 mg (1.57 eq.) (4-benzo[1,2,5]oxadiazol-5-yl-phenyl)-methyl-carbamic acid tert-butyl ester are dissolved in 10 mL dichloromethane, treated with 0.126 mL (1.05 eq.) trifluoroacetic acid and stirred overnight at room temperature. The reaction mixture is evaporated and the residue column chromatographed (hexane, hexane/ethyl acetate 4:1 then 3:1) to yield the desired product as an orange solid. MS(ES+): 226 (M+1).
$^1$H-NMR (CDCl$_3$, 400 MHz): delta (ppm)=7.82 (d, H$_{arom}$); 7.81 (s, H$_{arom}$), 7.71 (d, H$_{arom}$); 7.54, 6.72 (2d, 2×2H$_{arom}$); 2.92 (s, Me).

The starting material is obtained according to the procedure described in Example 7 from 5-bromo-benzo[1,2,5]oxadiazole and (4-bromo-phenyl)-methyl-carbamic acid tert-butyl ester, as a yellow powder.
$^1$H-NMR (CDCl$_3$, 400 MHz): delta (ppm)=7.84 (s, H$_{arom}$); 7.82, 7.63 (2d, 2H$_{arom}$); 7.54, 7.18 (2d, 2×2 H$_{arom}$); 3.26 (s, Me); 1.43 (s, tBu).

The following compounds of example 14 to 16 are prepared according to the same procedure:

EXAMPLE 14

(4Benzo[1,2,5]thiadiazol-5-yl-phenyl)-methyl-amine

Starting from (4-benzo[1,2,5]thiadiazol-5-yl-phenyl)-methyl-carbamic acid tert-butyl ester. MS(ES+): 242 (M+1).

The starting compound is obtained according to the procedure described in Example 7 from 5-bromo-benzo[1,2,5]thiadiazole and (4-bromo-phenyl)-methyl-carbamic acid tert-butyl ester, as a yellow powder.
$^1$H-NMR (CDCl$_3$, 400 MHz): delta (ppm)=8.08 (s, H$_{arom}$); 7.98, 7.80 (2d, 2H$_{arom}$); 7.60, 7.33 (2d, 2×2 H$_{arom}$); 3.26 (s, Me); 1.43 (s, tBu).

The starting material is obtained as follows:

a) (4-Bromo-phenyl)-methyl-carbamic acid tert-butyl ester 0.263 mL (1.1 eq.) iodomethane are added dropwise at room temperature to a stirred suspension of 1.1 g (4 mmol) (4-bromo-phenyl)-carbamic acid tert-butyl ester and 2 g (1.6 eq.) cesium carbonate in 15 mL DMF. After stirring for an additional 18 hours, the reaction mixture is extracted with water/ethyl acetate and the combined organic phases are washed with brine, dried over magnesium sulfate and evaporated to yield the desired product as a colorless oil, which is used without further purification.

b) (4-Bromo-phenyl)-carbamic acid tert-butyl ester 2 mL (1.2 eq.) Triethylamine are added to a solution of 2 g (11.6 mmol) p-bromo-aniline in 25 mL THF. The reaction mixture is cooled to 0° C. and treated with 2.66 g (1.05 eq.) Boc$_2$O under continuous stirring, then allowed to reach 20° C., stirred for an additional 20 hours and extracted with water/ethyl acetate. The combined organic phases are washed with brine, dried over magnesium sulfate and evaporated. The residue is column chromatographed (hexane, hexane/ethyl acetate 7:1 then 4:1) to yield after evaporation and recrystallization from hexane the desired product as a white powder.

EXAMPLE 15

(4Benzo[1,2,5]oxadiazol-5-yl-3-methoxy-phenyl)-methyl-amine

Starting from (4-Benzo[1,2,5]oxadiazol-5-yl-3-methoxy-phenyl)-methyl-carbamic acid tert-butyl ester.
$^1$H-NMR (CD$_3$OD, 400 MHz): delta (ppm)=7.78 (m, 3H$_{arom}$); 7.25 (d, H$_{arom}$); 6.38 (m, H$_{arom}$); 6.36 (m, H$_{arom}$); 3.83 (s, Me); 2.84 (s, Me).

The starting compound is obtained according to the procedure described in Example 7 from 5-bromo-benzo[1,2,5]oxadiazole and (4-bromo-3-methoxy-phenyl)-methyl-carbamic acid tert-butyl ester, as a yellow powder. MS(ES+): 378 (M+23).

The starting material is obtained as follows:

(4-Bromo-3-methoxy-phenyl)-methyl-carbamic acid tert-butyl ester 0.5 mL (1.1 eq.) iodomethane are added dropwise at room temperature to a stirred suspension of 2 g (6.6 mmol) (4-benzo[1,2,5]oxadiazol-5-yl-3-methoxy-phenyl)-methyl-carbamic acid tert-butyl ester and 3.2 g (1.5 eq.) cesium carbonate in 50 mL DMF. After stirring for an additional 17 hours, the reaction mixture is extracted with water/ethyl acetate and the combined organic phases are washed with brine, dried over magnesium sulfate and evaporated to yield the desired product as a yellow oil, which is used without further purification.

EXAMPLE 16

(4Benzo[1,2,5]oxadiazol-5-yl-3-methoxy-phenyl)-(2-fluoro-ethyl)-amine

Starting from (4-benzo[1,2,5]oxadiazol-5-yl-3-methoxy-phenyl)-(2-fluoro-ethyl)-carbamic acid tert-butyl ester.
$^1$H-NMR (CD$_3$OD, 400 MHz): delta (ppm)=7.78-7.84 (m, 3H$_{arom}$); 7.26 (d, H$_{arom}$); 6.44 (s, H$_{arom}$); 6.40 (d, H$_{arom}$); 4.68 (t, C$\underline{H}^2$F); 4.58 (t, C$\underline{H}_2$F); 3.82 (s, Me); 3.55 (t, C$\underline{H}_2$N); 3.46 (t, C$\underline{H}_2$N).

The starting compound is obtained according to the procedure described in Example 7 from 5-bromo-benzo[1,2,5]oxadiazole and (4-bromo-3-methoxy-phenyl)-(2-fluoro-ethyl)-carbamic acid tert-butyl ester, as a yellow glass. MS(ES+): 410 (M+23).

The starting material is obtained as follows:

(4-Bromo-3-methoxy-phenyl)-methyl-carbamic acid tert-butyl ester 0.63 mL (1.25 eq.) 1-bromo-2-fluoroethane are added at room temperature to a stirred suspension of 2 g (6.6 mmol) (4-benzo[1,2,5]oxadiazol-5-yl-3-methoxy-phenyl)-methyl-carbamic acid tert-butyl ester and 3.2 g (1.5 eq.) cesium carbonate in 50 mL DMF. After stirring for 12 hours at 50 to 55° C., the reaction mixture is cooled to rt. And extracted with water/ethyl acetate. The combined organic phases are washed with brine, dried over magnesium sulfate and evaporated to yield the desired product as a yellow oil, which is used without further purification.

EXAMPLE 17

(4Benzo[1,2,5]oxadiazol-5-yl-phenyl)-(2-fluoro-ethylmethyl-amine 220 mg (0.98 mmol) (4-benzo[1,2,5]oxadiazol-5-yl-phenyl)-methyl-amine are dissolved in 5 mL DMF, treated with 1.9 g (6 eq.) cesium carbonate, 320 mg (2 eq.) potassium iodide and 0.364 mL (5 eq.) 1-bromo-2-fluoroethane, and stirred for 20 hours at 50° C. The reaction mixture is extracted with water and ethyl acetate, the combined organic phases are washed with water and brine, dried over magnesium sulfate and evaporated. The residue is column chromatographed (gradient from hexane to ethyl acetate) to yield the desired product as an orange powder.

$^1$H-NMR (CDCl$_3$, 400 MHz): delta (ppm)=7.77 (d, H$_{arom}$); 7.75 (s, H$_{arom}$); 7.65 (d, H$_{arom}$); 7.51, 6.75 (2d, 2×2H$_{arom}$); 4.57, 3.67 (2m, 2CH$_2$); 3.04 (s, Me).

EXAMPLE 18

5-[3-(2-Fluoroethoxy)-phenyl]-Benzo[1,2,5]oxadiazole 600 mg (2.83 mmol) 3-benzo[1,2,5]oxadiazol-5-yl-phenol are dissolved in 15 mL DMF and stirred for 20 hours at room temperature in the presence of 1.15 g (1.25 eq.) cesium carbonate and 0.264 mL 1-bromo-2-fluoroethane. The reaction mixture is extracted with water and ethyl acetate, the combined organic phases are washed with water and brine, dried with magnesium sulfate and evaporated to dryness. The residue is column chromatographed (gradient from hexane to hexane/ethyl acetate 3:2) to yield the desired product as a pale yellow powder. MS(ES+): 259 (M+1).

$^1$H-NMR (CDCl$_3$, 400 MHz): delta (ppm)=7.95 (s, H$_{arom}$); 7.90 (d, H$_{arom}$); 7.70 (d, H$_{arom}$); 7.42 (m, H$_{arom}$); 7.27 (m, H$_{arom}$); 7.22 (s, H$_{arom}$); 7.04 (m, H$_{arom}$); 4.80, 4.31 (2m, 2CH$_2$).

The starting material 3-benzo[1,2,5]oxadiazol-5-yl-phenol is obtained according to the procedure described in Example 1 starting from 5-bromo-benzo[1,2,5]oxadiazole and 3-hydroxyphenylboronic acid, as a light yellow powder.

$^1$H-NMR (CDCl$_3$, 400 MHz): delta (ppm)=7.94 (s, H$_{arom}$); 7.92, 7.68 (2d, 2 H$_{arom}$); 7.38 (t, H$_{arom}$); 7.24 (d, H$_{arom}$); 7.13 (s, H$_{arom}$); 6.94 (d, H$_{arom}$); 4.93 (OH).

EXAMPLE 19

(2Benzo[1,2,5]oxadiazol-5-yl-thiazol-5-yl)-(2-fluoro-ethyl)-amine 53 mg (0.2 mmol) benzo[1,2,5]oxadiazole-5-carboxylic acid [(2-fluoro-ethylcarbamoyl)-methyl]-amide and 97 mg (1.2 eq.) Lawesson's reagent are suspended in 20 mL toluene and heated to reflux for one hour. After cooling to room temperature, the reaction mixture is poured onto ice-water containing 2 mL of a saturated aqueous solution of sodium carbonate, then extracted with ethyl acetate, The combined organic phases are dried with sodium sulfate and evaporated to dryness. The residue is column chromatographed (petroleum ether/ethyl acetate 3:2) to yield after evaporation of the corresponding fractions the desired product as an orange powder. MS (ES+): 265 (M+1).

$^1$H-NMR (CDCl$_3$, 400 MHz): delta (ppm)=8.12 (d, H$_{arom}$); 7.95 (s, H$_{arom}$); 7.82 (d, H$_{arom}$); 7.04 (s, H$_{het}$); 4.70, 3.53 (2m, 2CH$_2$).

The starting materials were obtained as follows:

a) Benzo[1,2,5]oxadiazole-5-carboxylic acid [(2-fluoro-ethylcarbamoyl)-methyl]-amide 221 mg (1 mmol) [(benzo[1,2,5]oxadiazole-5-carbonyl)-amino]-acetic acid, 120 mg (1.2 eq.) 2-fluoroethylamine, 162 mg (1.2 eq.) HOBt and 230 mg (1.2 eq.) EDC.HCl are dissolved in 18 mL DMF and cooled to 5° C. 0.7 mL (4 eq.) Hünig's base are added under stirring, the reaction mixture is stirred for an additional 3 hours at room temperature then extracted with water and ethyl acetate. The combined organic phases are washed with brine, dried with sodium sulfate and evaporated to yield the desired product as a beige solid. MS (ES+): 267 (M+1).

b) [(Benzo[1,2,5]oxadiazole-5-carbonyl)-amino]-acetic acid 500 mg (2.13 mmol) [(benzo[1,2,5]oxadiazole-5-carbonyl)-amino]-acetic acid methyl ester are treated in 50 mL methanol with 6 mL (3 eq.) 1N KOH in methanol containing 10% water at room temperature for two hours, then cooled below 5° C. and neutralized with 6 mL 1 N aqueous HCl. The reaction mixture is extracted with ethyl acetate, the combined organic phases are washed with brine and dried with sodium sulfate, then evaporated to dryness to yield the desired product as a beige-pinkish powder. MS (ES−): 220 (M−1)

c) [(Benzo[1,2,5]oxadiazole-5-carbonyl)-amino]-acetic acid methyl ester 492 mg (3 mmol) benzo[1,2,5]oxadiazole-5-carboxylic acid 376 mg (1 eq.) glycine methyl ester hydrochloride, 486 mg (1.2 eq.) HOBt and 690 mg (1.2 eq.) EDC.HCl are dissolved in 20 mL DMF under argon and the reaction mixture is stirred at room temperature for 90 minutes after addition of 2 mL (4 eq.) Hünig's base. The reaction mixture is poured onto ice and brine, and extracted with ethyl acetate. The combined organic phases are dried with sodium sulfate and evaporated to yield the desired product as a beige powder. MS (ES+): 236 (M+1).

EXAMPLE 20

(4Benzo[1,2,5]oxadiazol-5-yl-phenyl)-(2-fluoro-ethyl)-amine 391 mg (1 mmol) (4-benzo[1,2,5]oxadiazol-5-yl-phenyl)-(2-fluoro-ethyl)-carbamic acid benzyl ester are hydrogenated in the presence of Pd/C, the reaction mixture filtered through celite and evaporated to dryness. The residues is column chromatographed (dichloromethane/petroleum ether 8:2) to yield the desired product as a yellow powder. MS(ES+): 258 (M+1).

$^1$H-NMR (CDCl$_3$, 400 MHz): delta (ppm)=7.82 (d, H$_{arom}$); 7.81 (s, H$_{arom}$); 7.70 (d, H$_{arom}$); 7.53 (m, 2H$_{arom}$); 6.75 (m, 2H$_{arom}$); 4.66, 3.51 (2m, 2CH$_2$).

The starting material is obtained according to the procedure described in Example 1 from 5-benzo[1,2,5]oxadiazole-boronic acid and (4-bromo-phenyl)-(2-fluoro-ethyl)-carbamic acid benzyl ester, as a light brown resin. MS(ES+): 392 (M+1).

The starting compound can be synthesized as follows:

a) (4-bromo-phenyl)-(2-fluoro-ethyl)-carbamic acid benzyl ester 2.9 g (6 mmol) toluene-4-methanesulfonic acid 2-[benzyloxycarbonyl-(4-bromo-phenyl)-amino]-ethyl ester are dissolved in 100 mL THF and stirred for 18 hours at room temperature after addition of a 1 M solution of tetrabutylammonium fluoride in THF. The reaction mixture is poured onto ice and extracted with tertbutyl-methyl ether and a saturated aqueous solution of sodium bicarbonate. The combined organic phases are washed with brine, dried with sodium sulfate and evaporated to dryness. The crude product is column chromatographed (petroleum ether/ethyl acetate 4:1) to yield 920 mg desired product as a yellow resin. MS(ES+): 352 (M+1).

b) Toluene-4-methanesulfonic acid 2-[benzyloxycarbonyl-(4-bromo-phenyl)-amino]-ethyl ester 1.3 g (6 mmol) 2-(4-bromo-phenylamino)-ethanol are dissolved in 150 mL toluene, treated with 0.93 mL (1.1 eq.) benzyloxycarbonylchloride and 6.3 mL (1.05 eq.) 1N aqueous sodium hydroxide solution. The reaction mixture is stirred at room temperature for 18 hours, then the aqueous phase separated and extracted with ethyl acetate and water. The combined organic phases are washed with water and brine, then evaporated to dryness to yield 2.1 g crude (4-bromo-phenyl)-(2-hydroxy-ethyl)-carbamic acid benzyl ester, which is reacted further without additional purification by dissolution in 100 mL dichloromethane, addition of 5 mL (excess) pyridine, cooling to 5° C. and dropwise addition in 10 minutes of 2.45 g p-toluenesulfonic acid anhydride in 20 mL dichloromethane. The reaction mixture is stirred an additional 2 hours at room temperature and poured onto ice, then extracted at 10° C. with dichloromethane and an aqueous solution of sodium bicarbonate. The combined organic phases are dried with sodium sulfate and evaporated to yield the desired product as a light brownish resin, which is used without further purification.

EXAMPLE 21

(4Benzo[1,2,5]oxadiazol-5-yl-2-nitro-phenyl)-methyl-amine 140 mg (0.62 mmol) (4-benzo[1,2,5]oxadiazol-5-yl-phenyl)-methyl-amine are stirred at 0° C. in 2 mL concentrated sulfuric acid, then treated with 66 mg (1.05 eq.) potassium nitrate and stirred an additional 4 hours. The reaction mixture is poured onto ice, the precipitate filtered off, thoroughly washed with water and dried under high vacuum. The crude product is column chromatographed with ethyl acetate/petroleum ether 1:2 to yield after evaporation of the product-containing fraction the desired product as an orange solid. MS(ES−): 269 (M−1).
$^1$H-NMR (CDCl$_3$, 400 MHz): delta (ppm)=8.55 (s, H$_{arom}$); 8.22 (br.s, NH); 7.92 (d, H$_{arom}$); 7.91 (s, H$_{arom}$); 7.82 (d, H$_{arom}$); 7.72 (d, H$_{arom}$); 7.01 (d, H$_{arom}$); 3.13 (s, Me).

EXAMPLE 22

2Benzo[1,2,5]oxadiazol-5-yl-5-methylamino-phenol 100 mg (0.4 mmol) of (4-benzo[1,2,5]oxadiazol-5-yl-3-methoxy-phenyl)-methyl-amine are stirred at −10 to 0° C. in 1.3 mL of CH$_2$Cl$_2$, then over 5 minutes treated with 1.3 mL AlBr$_3$ (1.0 M solution in CH$_2$Br$_2$, 3 eq.) and stirred another 17 h under warming to rt. Then, the mixture is poured onto brine/ethyl acetate and the pH adjusted to 6 using NaHCO$_3$. Then the aqueous phase is extracted with ethyl acetate, the combined organic layers dried with sodium sulfate and concentrated. The crude product is column chromatographed with ethyl acetate/hexanes 1:1 to yield after evaporation of the product-containing fractions the desired product as a yellow solid.
$^1$H-NMR (CD$_3$OD, 400 MHz): delta (ppm)=7.88-7.94 (m, 2H$_{arom}$); 7.79 (d, H$_{arom}$); 7.24 (d, H$_{arom}$); 6.29 (d, H$_{arom}$); 6.21 (m, H$_{arom}$); 2.81 (s, Me).

EXAMPLE 23

2Benzo[1,2,5]oxadiazol-5-yl-5-(2-fluoro-ethylamino)-phenol 10 mg (0.03 mmol) of (4-benzo[1,2,5]oxadiazol-5-yl-3-methoxy-phenyl)-(2-fluoro-ethyl)-amine are dissolved in 0.3 mL acetic acid and 0.3 mL hydrobromic acid (33% in acetic acid) and stirred at 80 QC for 72 h. Then the solvents are removed. The mixture of starting material and desired product can be separated by HPLC (20 to 100% CH$_3$CN/H$_2$O (6'), 100% CH$_3$CN (1.5°), 100 to 20% CH$_3$CN/H$_2$O (0.5°): product elutes after 4.5°). MS(ES+): 274 (M+1).

EXAMPLE 24

(4Benzo[1,2,5]oxadiazol-5-yl-3-methoxy-phenyl)-dimethyl-amine 200 mg (0.8 mmol) of (4-benzo[1,2,5]oxadiazol-5-yl-3-methoxy-phenyl)-methyl-amine are stirred at 0 to 5° C. in 5 mL of DMF, then over 1 minute treated with 1 mL NaHMDS-solution (1.0 M, 1.25 eq.) and stirred another minute. Then, 0.5 mL (7.8 mmol, 10 eq.) of methyliodide is added and stirred 2 minutes under warming to rt. Then, the mixture is extracted with ethyl acetate/aqueous NaHCO$_3$, the combined organic layers dried with sodium sulfate and concentrated. This yields the desired product as a reddish-yellow solid.
$^1$H-NMR (CD$_3$OD, 400 MHz): delta (ppm)=7.80-7.84 (m, 2H$_{arom}$); 7.36 (d, H$_{arom}$); 6.50 (d, H$_{arom}$); 6.45 (m, H$_{arom}$); 3.90 (s, MeO); 3.08 (s, 2Me).

EXAMPLE 25

2Benzo[1,2,5]oxadiazol-5-yl-5-dimethylamino-phenol 140 mg (0.52 mmol) of (4-benzo[1,2,5]oxadiazol-5-yl-3-methoxy-phenyl)-dimethyl-amine are stirred at −10 to 0° C. in 1.7 mL of CH$_2$Cl$_2$, then over 5 minutes treated with 1.7 mL AlBr$_3$ (1.0 M solution in CH$_2$Br$_2$, 3.3 eq.) and stirred another 19 h under warming to rt. Then, the mixture is extracted with brine/ethyl acetate, the combined organic layers dried with sodium sulfate and concentrated. The crude product is column chromatographed with ethyl acetate/hexanes 1:4 to yield after evaporation of the product-containing fractions the desired product as a red solid.

1H-NMR (CD$_3$OD, 400 MHz): delta (ppm)=7.90-7.94 (m, 2H$_{arom}$); 7.80 (d, H$_{arom}$); 6.43 (d, H$_{arom}$); 6.38 (m, H$_{arom}$); 4.00 (s, 2Me).

EXAMPLE 26

Staining of APP23 Mouse and Human ALZHEIMER Disease (AD) Brain Sections Using an Agent of the Invention or Thioflavine S.

Four-micrometer thick paraffin sections from an APP23 mouse at 26 months of age are deparaffinized in xylene and rehydrated. 10 mg of the compound are dissolved in 1 mL DMSO and diluted with deionized water 1:10. This staining solution is applied on sections for about 20 min. Section background is cleared by washing with 95% ethanol. Finally sections are dehydrated in 99% ethanol, cleared in xylene and mounted with Vectashield™. Sections are investigated using fluorescence microscopy with the following filter combination: Excitation 450490 nm, emission 510 nm. Twenty micrometer thick cryotom sections from a AD brain cortex are air dried and fixated in 4% PFA for 5 min. After washing in tap water sections are stained either with Thioflavine S or with the compound for 5 min and further processed as described above. The compound is dissolved in DMSO and diluted to a final concentration of 0.01% with 50% Ethanol, Thioflavine S is dissolved in 50% Ethanol, final concentration is 0.01%.

Results:
(These results do not apply to the compounds of Examples 4, 5, 11, 12 and 21, which are not fluorescent)

1) Staining of APP23 Mice Brain Sections
The agents of the invention strongly stain amyloid deposits and vascular deposits in brain sections of APP23 mice.

2) Staining of Human AD Brain Sections:
Brain sections taken from frontal cortex of AD patients are stained with the agents of the invention, and the results compared with a Thioflavine S stain. The agents of the invention intensely and selectively stain amyloid deposits.

The invention claimed is:

1. A compound of formula I

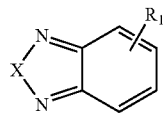

I wherein X is O or S, R$_1$ is 5-(2-fluoro-ethylamino)-thiazol-2-yl, 5-(2-$^{18}$F-ethylamino)-thiazol-2-yl or a group of formula (a)

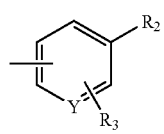

(a)

wherein Y is CH or N, R$_2$ is NHCH$_3$, NH$^{11}$CH$_3$, N(CH$_3$)$^{11}$CH$_3$, N(CH$_3$)$_2$, N($^{11}$CH$_3$)$_2$, NH(CH$_2$)$_n$F, NH(CH$_2$)$_n$$^{18}$F, N(CH$_3$)—(CH$_2$)$_n$F, N(CH$_3$)—(CH$_2$)$_n$$^{18}$F, O—(CH$_2$)$_n$F, O—(CH$_2$)$_n$$^{18}$F, CONH(CH$_2$)$_n$F or CONH(CH$_2$)$_n$$^{18}$F (n being in each case 2 to 4) and R$_3$ is hydroxy, (C1-4)alkoxy, hydrogen or nitro, in free base or acid addition salt form.

2. A process for the production of a compound of formula I as defined in claim 1 and its acid addition salts, comprising the steps of
a) for the production of a compound of formula I which contains no $^{11}$C or $^{18}$F atom, reacting a compound of formula II

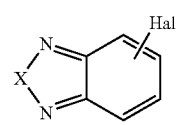

II wherein X is as defined in claim 1 and Hal is Cl, Br or I, with 5-(2-fluoro-ethylamino)thiazolyl-2-boronic acid or a compound of formula III

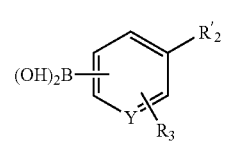

III wherein Y and R$_3$ are as defined above and R'$_2$ is a group R$_2$ as defined above which contains no $^{11}$C or $^{18}$F atom, or
b) for the production of a compound of formula I wherein R$_1$ is 5-(2-$^{18}$F-ethylamino)-thiazol-2-yl, reacting a compound of formula I wherein R$_1$ is 5-(2-mesyloxy-ethylamino)thiazol-2-yl or 5-(2-tosyloxy-ethylamino)-thiazol-2-yl with $^{18}$FΘ, or
c) for the production of a compound of formula I wherein R$_2$ is NH$^{11}$CH$_3$, N(CH$_3$)$^{11}$CH$_3$ or N($^{11}$CH$_3$)$_2$, reacting a compound of formula I wherein R$_2$ is NH$_2$ or NHCH$_3$ with $^{11}$CH$_3$I, or
d) for the production of a compound of formula I wherein R$_2$ is NH(CH$_2$)$_n$$^{18}$F, N(CH$_3$)—(CH$_2$)$_n$$^{18}$F, O—(CH$_2$)$_n$$^{18}$F or CONH(CH$_2$)$_n$$^{18}$F, reacting a compound of formula I wherein R$_2$ is, respectively, NH(CH$_2$)$_n$OTs or NH(CH$_2$)$_n$OMs, N(CH$_3$)—(CH$_2$)$_n$OTs or N(CH$_3$)—(CH$_2$)$_n$—OMs, O—(CH$_2$)$_n$OTs or O—(CH$_2$)$_n$—OMs, or CONH(CH$_2$)$_n$OTs or ONH(CH$_2$)$_n$OMs, with $^{18}$FΘ,
and recovering the resulting compound of formula I in free base form or acid addition salt form.

3. A composition for labeling histopathological structures in vitro or in vivo, comprising a compound of formula I as defined in claim 1, in free base or acid addition salt form.

4. A method for labeling histopathological structures in vitro or in vivo, comprising contacting brain tissue with a compound of formula I as defined in claim 1, in free base or acid addition salt form.

5. A method according to claim 4, for labeling β-amyloid deposits.

6. A method according to claim 4, comprising administering the compound of formula I to a patient.

7. A method according to any of claims 4, comprising the further step of determining whether the compound of formula I labeled the target structure.

8. A method according to claim 7, comprising observing the target structure labeled with a non-radioactive compound of formula I, using fluorescence microscopy.

9. A method according to claim 7, comprising observing the target structure labeled with a radioactive compound of formula I, using positron emission tomography (PET).

10. A method according to claim 4 for diagnosing Alzheimer's disease.

11. A method according to claim 10, for monitoring the effectiveness of a therapeutic treatment of Alzheimer's disease.

12. A method according to claim 4, for detecting histopathological hallmarks of Alzheimer's disease.

13. A package comprising a compound of formula I,

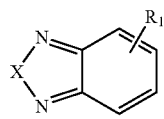

I wherein X is O or S, $R_1$ is 5-(2-fluoro-ethylamino)-thiazol-2-yl, 5-(2-$^{18}$F-ethylamino)-thiazol-2-yl or a group of formula (a)

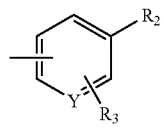

(a)

wherein Y is CH or N, $R_2$ is $NH_2$ or $NHCH_3$, and $R_3$ is hydroxy, (C1-4)alkoxy, hydrogen or nitro, in free base or acid addition salt form, together with instructions for the production of the compound of formula I wherein $R_2$ is $NH^{11}CH_3$, $N(CH_3)^{11}CH_3$ or $N(^{11}CH_3)_2$ by reaction of the starting material with freshly prepared $^{11}CH_3I$.

14. A package comprising as starting material a compound of formula I,

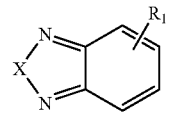

I wherein X is O or S, $R_1$ is 5-(2-fluoro-ethylamino)-thiazol-2-yl, 5-(2-$^{18}$F-ethylamino)-thiazol-2-yl or a group of formula (a)

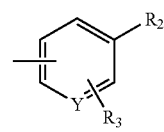

(a)

wherein Y is CH or N, $R_2$ is $NH(CH_2)_n OTs$, $NH(CH_2)_n OMs$, $N(CH_3)$—$(CH_2)_n OTs$, $N(CH_3)$—$(CH_2)_n OMs$, O—$(CH_2)_n OTs$, O—$(CH_2)_n OMs$, $CONH(CH_2)_n OTs$ or $ONH(CH_2)_n OMs$ (n being in each case 2 to 4), wherein OMs corresponds to mesylate and OTs to tosylate, and $R_3$ is hydroxy, (C1-4)alkoxy, hydrogen or nitro, in free base or acid addition salt form, together with instructions for the production of the compound of formula I wherein $R_2$ is $NH(CH_2)_n^{18}F$, $N(CH_3)$—$(CH2)_n^{18}F$, O—$(CH_2)_n^{18}F$ or $CONH(CH_2)_n^{18}F$ by a suitable reaction cascade of the starting material with $^{18}F\ominus$.

* * * * *